(12) United States Patent
Han et al.

(10) Patent No.: US 11,319,600 B2
(45) Date of Patent: May 3, 2022

(54) CUCUMBER MALE STERILITY GENE, MOLECULAR MARKER, SCREENING METHOD AND APPLICATION THEREOF

(71) Applicant: Tianjin Kernel Agricultural Science and Technology Corporation Ltd. Cucumber Research Institute, Tianjin (CN)

(72) Inventors: Yike Han, Tianjin (CN); Shengli Du, Tianjin (CN); Fengyue Zhao, Tianjin (CN); Aimin Wei, Tianjin (CN); Nan Liu, Tianjin (CN); Zhengwu Chen, Tianjin (CN); Xinmeng Fu, Tianjin (CN)

(73) Assignee: Tianjin Kernel Agricultural Science and Technology Corporation Ltd. Cucumber Research Institute, Tianjin (CN)

( * ) Notice: Subject to any disclaimer, the term of this patent is extended or adjusted under 35 U.S.C. 154(b) by 168 days.

(21) Appl. No.: 16/610,853

(22) PCT Filed: Jan. 12, 2018

(86) PCT No.: PCT/CN2018/072412
§ 371 (c)(1),
(2) Date: Nov. 4, 2019

(87) PCT Pub. No.: WO2018/201754
PCT Pub. Date: Nov. 8, 2018

(65) Prior Publication Data
US 2020/0407805 A1     Dec. 31, 2020

(30) Foreign Application Priority Data

May 5, 2017   (CN) .......................... 201710313270.1

(51) Int. Cl.
C12Q 1/68          (2018.01)
C12Q 1/6895      (2018.01)

(52) U.S. Cl.
CPC ...... *C12Q 1/6895* (2013.01); *C12Q 2531/113* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| CN | 102260338 A | 11/2011 |
|----|-------------|---------|
| CN | 103525917 A | 1/2014 |
| CN | 104120126 A | 10/2014 |
| CN | 105420408 A | 3/2016 |
| CN | 105525000 A | 4/2016 |
| CN | 107058552 A | 8/2017 |
| WO | WO 2016/086305 A1 | 6/2016 |

OTHER PUBLICATIONS

GenBank (2015) Reference Sequence XM_011654407.2, 3pp. (Year: 2015).*
Theoretical and Applied Genetics (2018) 131:449-460, including supplemental Fig S2. published online Nov. 13, 21017. (Year: 2017).*
International Search Report and Written Opinion dated Apr. 9, 2018, for International application No. PCT/CN2018/072412, from which the present application claims priority.
Liang (Published online Oct. 2016) "Map-based Cloning of the Dominant Genic Male Sterile Ms-cd1 Gene in Cabbage (*Brassica oleracea*)," Theoretical and Applied Genetics (Jan. 2017) 130, pp. 71-79.
Chinese First Office Action and Search Report with English translation, dated Apr. 1, 2020, in Chinese Patent Application No. 201710313270.1, 11 pp.
Han et al. (Nov. 2017) "Fine mapping of a male sterility gene ms-3 in a novel cucumber (*Cucumis sativus* L.) mutant," Theoretical and Applied Genetics (2018) 131:449-460, 12 pp.
Lu (2014) "QTL Mapping of Early Flowering Gene in Cucumber," Chinese Academy of Agricultural Sciences Dissertation, English abstract and p. 12: 4 pp.
GenBank (2015) "Predicted: Cucumis sativus PHD finger protein Male Meiocyte Death 1 (LOC101209218), mRNA" NCBI Reference Sequence XM_011654407.2, Available online at https://www.ncbi.nlm.nih.gov/nuccore/1784863903: 3 pp.

* cited by examiner

*Primary Examiner* — Juliet C Switzer
(74) *Attorney, Agent, or Firm* — Leydig, Voit & Mayer, Ltd.

(57) ABSTRACT

The invention relate to SNP and InDel markers associated with a cucumber male sterility gene and a screening method thereof. The cucumber male sterility gene is acquired by screening according to the markers. Specifically, the screening method includes following steps: (1) configuring groups; (2) building a library and sequencing; (3) adopting bulked segregation analysis (BSA); and (4) performing competitive allele specificity PCR (KASP), finely mapping a sterility gene, and acquiring SNP or InDel locus in close linkage with sterility character. The acquiring of the male sterility gene provides an effective tool for quick identification of cucumber male sterility plants and efficient production of cucumber hybrid species.

1 Claim, 5 Drawing Sheets
Specification includes a Sequence Listing.

| SNP Marker Name | Position on Chromosome | Allele X | Allele Y | Primer_allele X (5'-3')<br>Primer_allele Y (5'-3') | Primer_Common (3'-5') |
|---|---|---|---|---|---|
| C304430G | 304430 | C | G | AATTACATGAATAAGTGTTCGTAATTTCG (SEQ ID NO: 5)<br>AATTACATGAATAAGTGTTCGTAATTTCC (SEQ ID NO: 6) | AAACTTCAAGTTTAGGATAGAATCGGTTTGA (SEQ ID NO: 25) |
| G564531C | 564531 | G | C | GGTTTGGAATCTTGCTTGGCATTG (SEQ ID NO: 7)<br>GGTTTGGAATCTTGCTTGGCATTC (SEQ ID NO: 8) | CAATCAACCATATTCAGTTTAATCAACTAAACAAA (SEQ ID NO: 26) |
| A701466G | 701466 | A | G | ATCTAGAAACCAAATAAAAACTATAGCCAA (SEQ ID NO: 9)<br>CTAGAAACCAAATAAAAACTATAGCCAG (SEQ ID NO: 10) | AATTTAGTTTCAAAATTTGTTTATTAATAAAAATATACATCTCT (SEQ ID NO: 27) |
| G729940C | 729940 | G | C | GGAACCCCTTCTGAAGCTGTG (SEQ ID NO: 11)<br>GGAACCCCTTCTGAAGCTGTC (SEQ ID NO: 12) | GTAGCTATAAGAAAGGGCAGAGACC (SEQ ID NO: 28) |
| T785141C | 785141 | T | C | GGGTCACGCAGATGGGTATTGA (SEQ ID NO: 13)<br>GGTCACGCAGATGGGTATTGG (SEQ ID NO: 14) | TCCAATCACCCACTTCCTACAATTTATCG (SEQ ID NO: 29) |
| C974274G | 974274 | C | G | ATTTGGTTTCTTGATACTATCAATTATACC (SEQ ID NO: 15)<br>ATTTGGTTTCTTGATACTATCAATTATACG (SEQ ID NO: 16) | CAAATGTTGGACAACAACATGATATTTAGTAG (SEQ ID NO: 30) |
| T1031386G | 1031386 | T | G | TACGTGAATATTTTCTTTTTCTTTATACGTAT (SEQ ID NO: 17)<br>CGTGAATATTTTCTTTTTCTTTATACGTAG (SEQ ID NO: 18) | ATTTAGAAAACACACGTATCAAAATTAACTTAGC (SEQ ID NO: 31) |
| T1101289C | 1101289 | T | C | AAGACTAATATGCCCTTCCTCTTCTA (SEQ ID NO: 19)<br>GACTAATATGCCCTTCCTCTTCTG (SEQ ID NO: 20) | ATTCCAAGTTGGGATTGAATGGAAATGG (SEQ ID NO: 32) |
| T1508343G | 1508343 | T | G | TATGTACAGCATCAACAAGTGTGCA (SEQ ID NO: 21)<br>TGTACAGCATCAACAAGTGTGCC (SEQ ID NO: 22) | ATCATCTGTCTCCAATTCACTTGAAAACTTT (SEQ ID NO: 33) |
| A2179014C | 2179014 | A | C | TTCGAACATATACAAAAGTAGATATATCAAAA (SEQ ID NO: 23)<br>CGAACATATACAAAAGTAGATATATCAAAC (SEQ ID NO: 24) | GTGATTCATTGAGAATATCTATTTAATTGTACTTG (SEQ ID NO: 34) |

FIG. 2

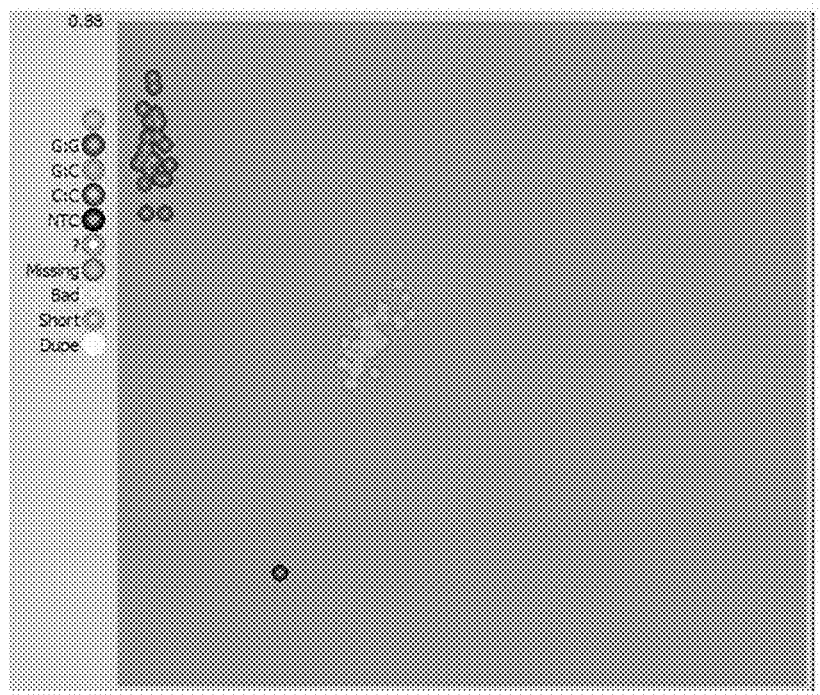
(a)
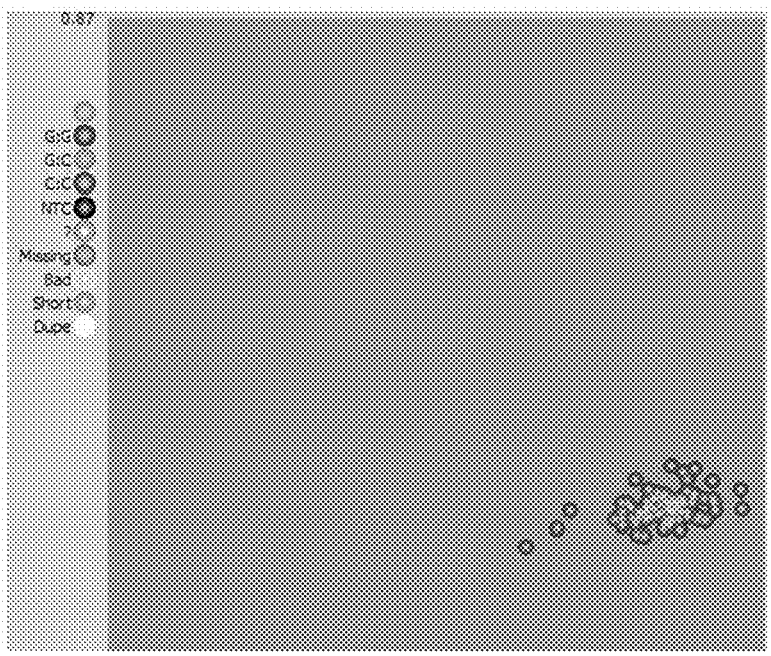
(b)
FIG.3

| Gene ID | Position on Chromosome | Gene Function |
|---|---|---|
| Csa3M006660.1 | Chr3-805509-807682 | Zinc Finger Protein Containing PHD Domain |

CDS sequence (SEQ ID NO: 1):
ATGTCGATTTCGATTCTGGAATCCTGCAAGAAGAGAAAAAGAAGGCCTAAACTTTTCGGGTTTCAAACGTTCGGGGA
TCCTGGATCGCCAATCAACCCCACGGGTCCATTTCGTGAGAATATCAGAATCTTTCTTCAACAATGTGCAGAGATTGA
AGATTACAGAATTCAAGAAATGCCTATATGGTGTACTCTCCTTGTTCATGAAAATAAAAGCTTCGTTGTTCCACTTTACA
CTATTGAAGAAGATGTGAAGCTCTCCCCAAAACCCTACTGCGATCAATGCCGATGTTCTGGGTGGAGTAATCATTTTG
TATCGAAAAGAAAATATCATATCGTAATACCGTTGGATGATCGGTGGAACAAACGATTAGACGATGGCGGTTTCGACC
TCGATGATCAAACTCATCTTCTTCATGGATTGATTCACTGCAATGGCTTCGGGCATTTGCTCTGCGTCAATGGAATCGA
AGGAGGATCCAAGTTTCTTTGTGGCAGAGAAGTTATGGATCTTTGGGATAGAATCTGCACAAATCTAAGAACAAGGA
AAATTACAGTTGAGGATTTATCCAAGAAACGATCAATGGATCTACGTCTTCTTCATGGGGTAGCATACGGTCATCCATG
GTTTGGGAGATGGGGCTACAGATTTTGCCGAGGAAGCTTTGGAGTGAAAGAACACCATTACAGTAGAGCTTTGGAA
ATCCTCAGCTCTCTGGAACTCGACAAGATAATGCACGAAGTCGACTATAGCGATCGAGGAAGAGAAGTGAAGCAAAT
CATTCGACATTATCGAAATCTGAGTGAAACGCAGTTGATCACACTGAAAGATCTACTGAAGTTCATGTTGACAGTAAA
ATATGTTTCTGCGATCGAGAAGAAAACGGTTCAACCAATCGCTAAATCTCCTCCTCCGTGTAGACAATCTCTGCAGCG
AAACAAGCAGCAATCTCTAGTGAAGGAGAAGCAAATACGGTACAGAAAATTCGCCACTGCAATTTCTAATATGGACA
GCCGATGGCCGGCGAGACGGTTAGAATACGCAGCGGAGGTGATTGTGAAAGCATTGGAAGAGAAGAAATCAGATA
AATTCAGCCATGGCGGAAATGGAATGACTCGTCAAGATGTTCGAGATGCTGCTCGCCTTCACATCGGCGACACTGGA
TTGCTCGATTACGTTCTAAAATCACTGAACAACGTGATCGTAGGTAACCAAATAGTTCGCCGTGCAGTGAATCCTAAA
ACACGAATTTTAGAGTACACGATTCATGAACTTAGAAATGGCATTCAATTAACAGAAGAGCAAGAATCAACAGAAAA
TTCAGAACCAACCGTAACTCCTGGCAAAGACATTTACAACGACGTGCTATGTATATACAGAAGCATTTTCCTTGACTAT
CCAGAATCAGAAATGGTAGAATTAGCAACCCAGGGAGTTCTCGATAGTAAACATTTTGCTAAAGAATGGCCTCTTCAA
GATGAAGAAGAGCATCTATTGACGTTCATTATCAAATTGATGCCGAGGCTAACTTTTACACATACGGATTTAGAGTTGA
AGAGTGATTTCATGCCATCCGGCGAGGTAGTGGTTCTTCCACTACACACAACAATCGGAGAAGTAAAAGAAGCAGC
AGAAAAAGCTCTAAGAGACACATATTACGTTACGGAACAGTTCGAGGTTTTGGCGATAGAGAATTTGGAGAATTACG
AAGACAGAGAGGTGATTTTTGGAGCGGTAGAATCGGGAGCAGAGTTGTTTGTGAAAGGAATGGGTATTGATTTAGA
TACACCATTGAAGTACCAAGGAGGAGTTGGTACATGGAAAGTTCGATGTGAGTGTGGCACCGGAGACGACGATGGC
GAGAGGATGGTGGCTTGTGACATATGCGAGATCTGGCAGCACACTCGCTGCTGTGGAATCGACGACGCTGATAATGT
GCCGTTGTTGTTCGTATGCGCCGCCTGCTGCGACTCGCTTGGACAATTAAAAATTTGA

FIG. 5

CUCUMBER MALE STERILITY GENE, MOLECULAR MARKER, SCREENING METHOD AND APPLICATION THEREOF

CROSS-REFERENCE TO RELATED APPLICATIONS

This application is a U.S. National Stage Application filed under 35 U.S.C. § 371 of International Application No. PCT/CN2018/072412, filed Jan. 12, 2018, which claims the benefit of Chinese Application No. 201710313270.1, filed May 5, 2017. Both of these applications are hereby incorporated by reference in their entireties.

TECHNICAL FIELD

The present disclosure relates to the technical field of molecular genetic breeding, in particular, to SNP or InDel markers associated with cucumber male sterility genes, a screening method thereof, and the obtained male sterility genes and their use in identifying male sterile plants.

BACKGROUND OF THE INVENTION

At present, many male sterility genes have been identified in other crops, and many markers closely linked to male sterility genes have been developed. However, there are few reports on cucumber male sterility genes, let alone applications thereof. In addition, nuclear-cytoplasmic male sterile lines, photosensitive male sterile lines and temperature-sensitive male sterile lines are most commonly used, while nuclear sterility genes are rarely used, mainly because it is difficult to find a maintainer line. The traditional method of gene mapping comprises isolating a large number of screening differential bands in the population with the existing molecular markers. In this case, mapping genes is too time-consuming and very laborious.

Although the patent application CN105420408A has explored the molecular markers of cucumber sterility genes, only one SNP marker has been obtained. However, the SNP marker is too solitary to map the cucumber sterility genes.

SUMMARY OF THE INVENTION

In an embodiment of this application, it relates to a method for obtaining a molecular marker, or a SNP or InDel marker, for plant male sterility and a method for mapping male sterility genes. The method comprises the following steps of:

(1) population preparation: crossing a male sterile line of plant as female parent with a genetically distinct fertile breed as male parent to obtain an F1 hybrid, and subjecting the F1 hybrid to selfing to obtain a segregating population of F2 generation, which comprises two phenotypes, namely a male fertility phenotype and a male sterility phenotype;

(2) pool construction and sequencing: extracting genomic DNAs of the female parent, the male parent, and fertile individuals and sterile individuals in the F2 generation; separately mixing the extracted genomic DNAs into four mixed pools, namely a female parent pool, a male parent pool, a fertile pool and a sterile pool; subjecting the genomic DNAs of each of the mixed pools to paired-end sequencing; aligning reads obtained by sequencing to normal cucumber genome by Burrows-Wheeler alignment (BWA) software; and conducting SNP detection and annotation with GATK software based on the alignment results;

(3) Bulked Segregant Analysis (BSA): calculating Δ(SNP-index) values between the fertile pool and the sterile pool based on the SNP detection results obtained by sequencing; and determining a region where a target gene is located by using 99% confidence interval of the Δ(SNP-index) values, wherein, a SNP-index value refers to a ratio of the number of reads containing SNP at a chromosomal locus to the total number of reads detected at the locus, and the Δ(SNP-index) values refer to the differences of the SNP-index values between the fertile pool and the sterile pool (Takagi et al., 2013);

(4) Kbioscience allele-specific PCR (KASP): performing KASP genotyping with SNP genotyping primers designed for candidate SNP site selected in candidate regions in 938 plants of the F2 population, to obtain a SNP or InDel site closely linked to sterility traits; and (5) constructing a genetic map based on the KSAP genotyping results and mapping the male sterile genes.

This study introduces parameter SNP-index values related to the sequencing depth of the SNP site, and the parameter refers to a ratio of the number of reads containing a SNP at a locus to the total number of reads detected at the locus, ranging from 0 to 1. If the parameter is 0, it means that all the detected reads are from the parental genome used as the reference genome; if this parameter is 1, it means that all reads are from the other parental genome; and if the parameter is 0.5, it means that the SNP in the mixed pool is identical in frequency from the two parental genomes. The SNP-index value is calculated for a SNP observed in both of the two pools, then Δ(SNP-index) value is obtained through subtraction of the SNP-index values between the two pools; a graph is generated in which the Δ(SNP-index) values correspond to the chromosomes on which the SNPs are located; and candidate genomic regions for male sterility are screened by using 99% confidence interval of the Δ(SNP-index) values. A null hypothesis is made for the Δ(SNP-index) values to obtain a corresponding p-value, which is used to test the confidence level of the Δ(SNP-index) values. Generally, $p<0.05$ is considered statistically significant.

In an embodiment of the disclosure, the plant is cucumber.

In an embodiment of the disclosure, the molecular marker is a SNP marker.

In an embodiment of the disclosure, the molecular marker is an InDel marker.

In an embodiment of the disclosure, the molecular marker is a SNP marker and an InDel marker.

In an embodiment of the disclosure, the male sterility gene is located in a genomic fragment between SNP marker G729940C and SNP marker C974274G.

In an embodiment of the disclosure, the male sterility gene is located on cucumber chromosome 3.

In an embodiment of the disclosure, the male sterility gene is located at positions 805,509-807,682 on cucumber chromosome 3.

In an embodiment of the disclosure, the gene for controlling cucumber male sterility is the Csa3M006660.1 gene represented by SEQ ID NO: 1, which encodes a protein of an amino acid sequence as represented by SEQ ID NO: 2.

In an embodiment of the disclosure, a point mutation occurs at position 1258 of the Csa3M006660.1 gene of the cucumber sterile line.

In an embodiment of the disclosure, the nucleic acid sequence of the Csa3M006660.1 gene of the cucumber sterile line is represented by SEQ ID NO: 3, which encodes a protein of an amino acid sequence represented by SEQ ID NO: 4.

In an embodiment of the disclosure, the SNP genotyping primers used for Kbioscience allele-specific PCR (KASP) are shown below:

the primers for C304430G marker:
(SEQ ID NO: 5)
AATTACATGAATAAGTGTTCGTAATTTCG
and (SEQ ID NO: 6)
AATTACATGAATAAGTGTTCGTAATTTCC;

the primers for G564531C marker:
(SEQ ID NO: 7)
GGTTTGGAATCTTGCTTGGCATTG
and (SEQ ID NO: 8)
GGTTTGGAATCTTGCTTGGCATTC the primers for A701466G marker:
(SEQ ID NO: 9)
ATCTAGAAACCAAATAAAAACTATAGCCAA
and (SEQ ID NO: 10)
CTAGAAACCAAATAAAAACTATAGCCAG the primers for G729940C marker:
(SEQ ID NO: 11)
GGAACCCCTTCTGAAGCTGTG
and (SEQ ID NO: 12)
GGAACCCCTTCTGAAGCTGTC the primers for T785141C marker:
(SEQ ID NO: 13)
GGGTCACGCAGATGGGTATTGA
and (SEQ ID NO: 14)
GGTCACGCAGATGGGTATTGG the primers for C974274G marker:
(SEQ ID NO: 15)
ATTTGGTTTCTTGATACTATCAATTATACC
and (SEQ ID NO: 16)
ATTTGGTTTCTTGATACTATCAATTATACG the primers for T1031386G marker:
(SEQ ID NO: 17)
TACGTGAATATTTTCTTTTTCTTTATACGTAT
and (SEQ ID NO: 18)
CGTGAATATTTTCTTTTTCTTTATACGTAG the primers for T1101289C marker:
(SEQ ID NO: 19)
AAGACTAATATGCCCTTCCTCTTCTA
and (SEQ ID NO: 20)
GACTAATATGCCCTTCCTCTTCTG the primers for T1508343G marker:
(SEQ ID NO: 21)
TATGTACAGCATCAACAAGTGTGCA
and (SEQ ID NO: 22)
TGTACAGCATCAACAAGTGTGCC -continued the primers for A2179014C marker:
(SEQ ID NO: 23)
TTCGAACATATACAAAAGTAGATATATCAAAA
and (SEQ ID NO: 24)
CGAACATATACAAAAGTAGATATATCAAAC.

An embodiment of the present disclosure relates to a method for identifying a sterile cucumber plant and a fertile cucumber plant, wherein if the base at position 1258 of the Csa3M006660.1 gene is G, the plant is a sterile plant.

The present disclosure has identified 10 SNP markers which are closely linked to the cucumber male sterility genes, wherein 6 of the SNP markers are more closely linked to the cucumber male sterility gene. The present disclosure has identified for the first time that the cucumber male sterility gene is the Csa3M006660.1 gene located on cucumber chromosome 3. The sterility gene identified by the present disclosure can be used for recognizing male sterile cucumber plants more directly and quickly, and can be used for efficient production of cucumber hybrids.

BRIEF DESCRIPTION OF THE FIGURES

FIG. 2 shows candidate SNP markers and their corresponding primers for KASP genotyping.

FIG. 3 shows KASP genotyping results for the C974274G marker: (a) shows KASP genotyping results for the fertile individuals; (b) shows KASP genotyping results for the sterile individuals.

FIG. 5 shows the nucleic acid sequence of the obtained Csa3M006660.1 gene.

DETAILED DESCRIPTION OF THE INVENTION

The specific embodiments of the present disclosure are specifically described with reference to the accompanying drawings and the following examples.

Example 1

The SNP molecular markers and sterility genes associated with cucumber male sterility traits were obtained by the following steps:

(1) Population Preparation: the male sterile line of "YL-5" as female parent was crossed with the genetically distinct breed "D37-1" as male parent to obtain an F1 hybrid, and the F1 hybrid was selfed to obtain a segregating population of F2 generation, which comprise two phenotypes, namely a male fertile phenotype and a male sterility phenotype;

(2) Pool Construction and Sequencing: after phenotype identification, genomic DNAs of the female parent "YL-5", the male parent "D37-1", and fertile individuals and sterile individuals in the F2 generation were extracted by CTAB method, and a total of four mixed pools were formed, namely a female parent pool, a male parent pool, a fertile pool and a sterile pool. The qualified DNA samples were paired-ended sequenced via the Illumina HiSeq 2500 platform; the raw reads obtained by sequencing were evaluated for quality and filtered to obtain clean and impurity-free reads, which were then aligned to the cucumber reference genome via the Burrows-Wheeler alignment (BWA) software; and the SNP detection and annotation was conducted using the GATK software based on the alignment results.

Figure 1:
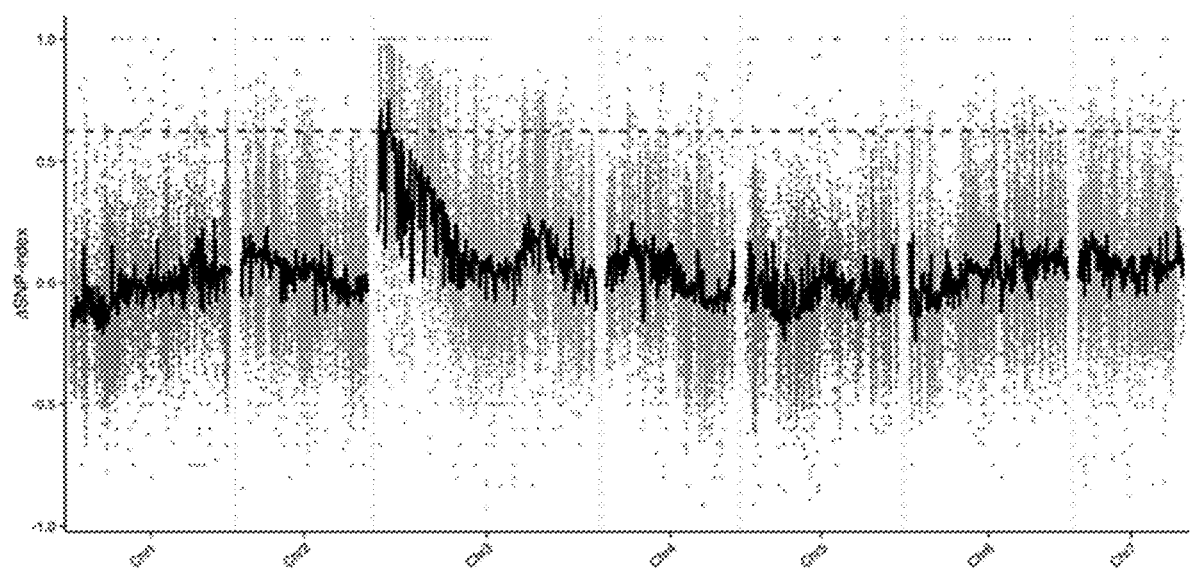
FIG. 1 shows the distribution of the Δ(SNP-index) values between the fertile pool and the sterile pool on 7 cucumber chromosomes via Bulked Segregant Analysis (BSA).

(3) Bulked Segregant Analysis (BSA): Δ(SNP-index) values between the fertile pool and the sterile pool were calculated based on the SNP detection results by means of a ratio of the number of reads of mutant genotype covering the locus to the total number of reads covering the locus. For example, if the number of reads covering a certain locus is 20, and the number of reads of the mutant genotype is 15, then the SNP-index value of the locus is 0.75; if SNP-index=0, then the reads are from the male parent "D37-1", and if SNP-index=1, then the reads are from the female parent "YL-5". Then the Δ(SNP-index) values between the fertile pool and the sterile pool were calculated and a Δ(SNP-index) graph was obtained (FIG. 1). Assuming that locus A is the locus where the target gene is located, then the SNP-index value at the locus is 0 for the fertile pool (the actual value is generally greater than 0 and less than 1 because there is the heterozygous genotype in the fertile pool), and is 1 for the sterile pool, and, accordingly, Δ(SNP-index)=1. Thus, the larger the Δ(SNP-index) value is, the more likely the target gene is. In this study, 99% confidence interval of the Δ(SNP-index) value was used to determine the locus where the target gene is located. The results showed that a significant segregation trend occurring only in a range of 813 Kb at the end of chromosome 3 (region 1: 166710-564531, 397 Kb; and region 2: 1954776-2371279, 416 Kb) between the fertile pool and the sterile pool.

(4) Kbioscience Allele-Specific PCR (KASP) Genotyping: 10 SNP sites were selected, and primer design for the same was performed using the method of Leal-Bertioli et al. (2015), which is a technique for genotyping SNPs and detecting insertion and deletion (InDels) based on the specific pairing of bases at the end of the primer. 10 sets of SNP genotyping primers in total were designed for the 10 SNP sites (FIG. 2), and KASP genotyping was performed in 948 plants of the F2 population. The genotypes of the corresponding sites were detected for genotyping in 948 plants of the F2 segregating population. Some results are shown in FIG. 3: the figure is the KASP genotyping graph of the C974274G marker, wherein FIG. 3(a) shows the genotyping of the C974274G marker in 96 fertile individuals, i.e., MF1 to MF-96; and FIG. 3(b) shows the genotyping of the C974274G marker in 96 sterile individuals, i.e., MS-1 to MS-96; each point in the figure corresponds to an individual plant: red indicates that the gene of this individual plant only carries the EXC tag sequence, i.e., the genotype of the site being G/G, blue indicates that the gene of the individual plant only carries the FAM tag sequence, i.e., the genotype of the site being C/C, green indicates the gene of the individual plant carries both the EXC tag sequence and the FAM tag sequence, i.e., the genotype of the site being heterozygous G/C, and black indicates not identified; in addition, only the genotyping results from the primers which can make the individuals of the three genotypes be clustered separately are useful. It can be seen from FIG. 3(a) that almost all of the 96 fertile plants, except one that was not identified successfully, were successfully genotyped. It can be seen from FIG. 3(b) that all of the 96 sterile plants were successfully genotyped. In addition, in the two genotyping results, the clustering of the individual plants of the three genotypes was good and thus the results were useful.

Figure 4:
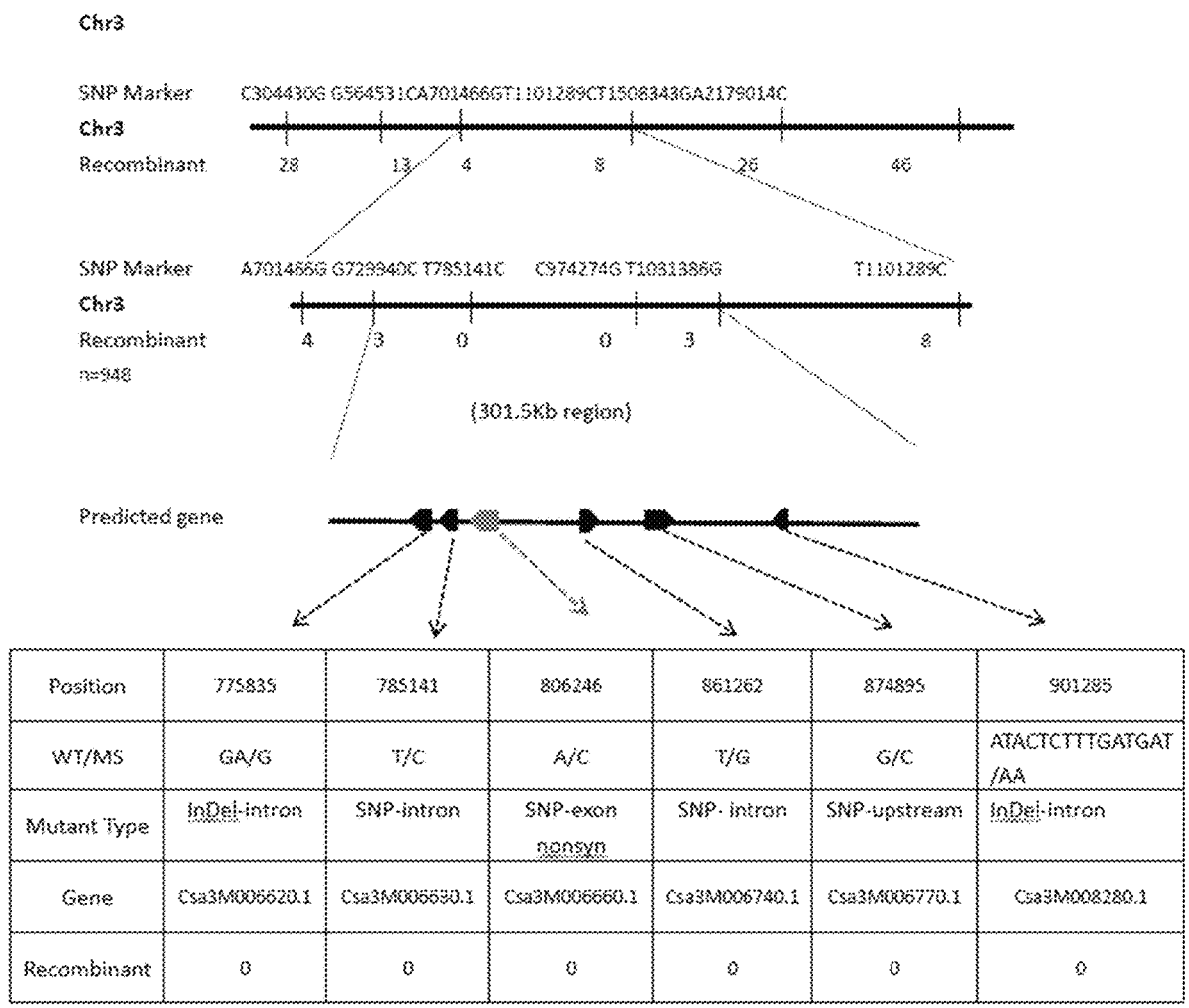
FIG. 4 shows a genetic map constructed by SNP markers and fine mapping of mutant genes.

A genetic map (FIG. 4) was constructed based on the genotyping results, and the sterility genes were finely mapped, and the SNP or InDel site closely linked to sterility was obtained. The final mapped gene was Csa3M006660.1 (FIG. 5), with six SNP or InDel sites closely linked to sterility traits.

(5) Sequence and Expression Analysis: it was found by amino acid sequence analysis that the Csa3M006660.1 protein has a typical PHD structure (Cys4HisCys3), which is a phylogenetically conserved zinc finger domain in eukaryotes and is capable of specifically recognizing the histone code for methylation.

It was found from homology alignment of amino acid sequences of different species and sequence analysis of 28 genetically distinct cucumber lines that the amino acid at position 420 of the Csa3M006660.1 protein is highly conserved, which is tyrosine (Y) in fertile plants and aspartic acid (D) in sterile plants. In other words, a point mutation from T to G occurs at position 1258 of the Csa3M006660.1 gene of the cucumber sterile line.

BLAST analysis revealed that the Csa3M006660.1 protein has 49.8% sequence homology with *Arabidopsis thaliana* MMD1, and they share the same amino acid type at position 420, and have the PHD domain. Many documents have reported that *Arabidopsis thaliana* MMD1 mutations lead to male sterility and may regulate the meiosis of pollen mother cells.

Expression pattern analysis of Csa3M006660.1 revealed that the gene is only expressed in young flower buds.

Example 2

Validation of Sterile Genes

The applicant randomly selected 100 fertile cucumber plants and 100 sterile cucumber plants. Primers were designed for SEQ ID NO: 1. The genomes of these plants were subjected to PCR amplification and sequencing. The results showed that the nucleic acid sequences amplified from all of the fertile plants have a T base at position 1258, and the nucleic acid sequences amplified from all of the sterile plants have a G base at position 1258.

What is claimed is:

1. A cucumber male sterile gene comprising a nucleic acid sequence comprising SEQ ID NO: 3.

* * * * *

SEQUENCE LISTING

<160> NUMBER OF SEQ ID NOS: 34

<210> SEQ ID NO 1
<211> LENGTH: 1995
<212> TYPE: DNA
<213> ORGANISM: Cucumis sativus

<400> SEQUENCE: 1

```
atgtcgattt cgattctgga atcctgcaag aagagaaaaa gaaggcctaa acttttcggg      60
tttcaaacgt tcggggatcc tggatcgcca atcaacccca cgggtccatt tcgtgagaat     120
atcagaatct ttcttcaaca atgtgcagag attgaagatt acagaattca agaaatgcct     180
```

```
atatggtgta ctctccttgt tcatgaaaat aaaagcttcg ttgttccact ttacactatt      240
gaagaagatg tgaagctctc cccaaaaccc tactgcgatc aatgccgatg ttctgggtgg      300
agtaatcatt ttgtatcgaa aagaaaatat catatcgtaa taccgttgga tgatcggtgg      360
aacaaacgat tagacgatgg cggtttcgac ctcgatgatc aaactcatct tcttcatgga      420
ttgattcact gcaatggctt cgggcatttg ctctgcgtca atggaatcga aggaggatcc      480
aagtttcttt gtggcagaga agttatggat ctttgggata gaatctgcac aaatctaaga      540
acaaggaaaa ttacagttga ggatttatcc aagaaacgat caatggatct acgtcttctt      600
catggggtag catacggtca tccatggttt gggagatggg gctacagatt ttgccgagga      660
agctttggag tgaaagaaca ccattacagt agagctttgg aaatcctcag ctctctggaa      720
ctcgacaaga taatgcacga agtcgactat agcgatcgag aagagaagt gaagcaaatc       780 attcgacatt atcgaaatct gagtgaaacg cagttgatca cactgaaaga tctactgaag      840
ttcatgttga cagtaaaata tgtttctgcg atcgagaaga aaacggttca accaatcgct      900
aaatctcctc ctccgtgtag acaatctctg cagcgaaaca agcagcaatc tctagtgaag      960
gagaagcaaa tacggtacag aaaattcgcc actgcaattt ctaatatgga cagccgatgg     1020
ccggcgagac ggttagaata cgcagcggag gtgattgtga aagcattgga agagaagaaa     1080
tcagataaat tcagccatgg cggaaatgga atgactcgtc aagatgttcg agatgctgct     1140
cgccttcaca tcggcgacac tggattgctc gattacgttc taaaatcact gaacaacgtg     1200
atcgtaggta accaaatagt tcgccgtgca gtgaatccta aaacacgaat tttagagtac     1260
acgattcatg aacttagaaa tggcattcaa ttaacagaag agcaagaatc aacagaaaat     1320
tcagaaccaa ccgtaactcc tggcaaagac atttacaacg acgtgctatg tatatacaga     1380 agcatttttcc ttgactatcc agaatcagaa atggtagaat tagcaaccca gggagttctc     1440
gatagtaaac attttgctaa agaatggcct cttcaagatg aagaagagca tctattgacg     1500
ttcattatca aattgatgcc gaggctaact tttacacata cggatttaga gttgaagagt     1560
gatttcatgc catccggcga ggtagtggtt cttccactac acacaacaat cggagaagta     1620
aaagaagcag cagaaaaagc tctaagagac acatattacg ttacggaaca gttcgaggtt     1680
ttggcgatag agaatttgga gaattacgaa gacagagagg tgattttttgg agcggtagaa     1740 tcgggagcag agttgtttgt gaaaggaatg ggtattgatt tagatacacc attgaagtac     1800
caaggaggag ttggtacatg gaaagttcga tgtgagtgtg gcaccggaga cgacgatggc     1860
gagaggatgg tggcttgtga catatgcgag atctggcagc acactcgctg ctgtggaatc     1920
gacgacgctg ataatgtgcc gttgttgttc gtatgcgccg cctgctgcga ctcgcttgga     1980
caattaaaaa tttga                                                      1995
```

<210> SEQ ID NO 2
<211> LENGTH: 664
<212> TYPE: PRT
<213> ORGANISM: Cucumis sativus

<400> SEQUENCE: 2

Met Ser Ile Ser Ile Leu Glu Ser Cys Lys Lys Arg Lys Arg Arg Pro
1               5                   10                  15

Lys Leu Phe Gly Phe Gln Thr Phe Gly Asp Pro Gly Ser Pro Ile Asn
            20                  25                  30

Pro Thr Gly Pro Phe Arg Glu Asn Ile Arg Ile Phe Leu Gln Gln Cys
        35                  40                  45

```
Ala Glu Ile Glu Asp Tyr Arg Ile Gln Glu Met Pro Ile Trp Cys Thr
 50                  55                  60
Leu Leu Val His Glu Asn Lys Ser Phe Val Val Pro Leu Tyr Thr Ile
 65                  70                  75                  80
Glu Glu Asp Val Lys Leu Ser Pro Lys Pro Tyr Cys Asp Gln Cys Arg
                 85                  90                  95
Cys Ser Gly Trp Ser Asn His Phe Val Ser Lys Arg Lys Tyr His Ile
                100                 105                 110
Val Ile Pro Leu Asp Asp Arg Trp Asn Lys Arg Leu Asp Asp Gly Gly
            115                 120                 125
Phe Asp Leu Asp Asp Gln Thr His Leu Leu His Gly Leu Ile His Cys
130                 135                 140
Asn Gly Phe Gly His Leu Leu Cys Val Asn Gly Ile Glu Gly Gly Ser
145                 150                 155                 160
Lys Phe Leu Cys Gly Arg Glu Val Met Asp Leu Trp Asp Arg Ile Cys
                165                 170                 175
Thr Asn Leu Arg Thr Arg Lys Ile Thr Val Glu Asp Leu Ser Lys Lys
                180                 185                 190
Arg Ser Met Asp Leu Arg Leu Leu His Gly Val Ala Tyr Gly His Pro
            195                 200                 205
Trp Phe Gly Arg Trp Gly Tyr Arg Phe Cys Arg Gly Ser Phe Gly Val
210                 215                 220
Lys Glu His His Tyr Ser Arg Ala Leu Glu Ile Leu Ser Ser Leu Glu
225                 230                 235                 240
Leu Asp Lys Ile Met His Glu Val Asp Tyr Ser Asp Arg Gly Arg Glu
                245                 250                 255
Val Lys Gln Ile Ile Arg His Tyr Arg Asn Leu Ser Glu Thr Gln Leu
            260                 265                 270
Ile Thr Leu Lys Asp Leu Leu Lys Phe Met Leu Thr Val Lys Tyr Val
            275                 280                 285
Ser Ala Ile Glu Lys Lys Thr Val Gln Pro Ile Ala Lys Ser Pro Pro
290                 295                 300
Pro Cys Arg Gln Ser Leu Gln Arg Asn Lys Gln Ser Leu Val Lys
305                 310                 315                 320
Glu Lys Gln Ile Arg Tyr Arg Lys Phe Ala Thr Ala Ile Ser Asn Met
                325                 330                 335
Asp Ser Arg Trp Pro Ala Arg Arg Leu Glu Tyr Ala Ala Glu Val Ile
                340                 345                 350
Val Lys Ala Leu Glu Glu Lys Lys Ser Asp Lys Phe Ser His Gly Gly
            355                 360                 365
Asn Gly Met Thr Arg Gln Asp Val Arg Asp Ala Ala Arg Leu His Ile
370                 375                 380
Gly Asp Thr Gly Leu Leu Asp Tyr Val Leu Lys Ser Leu Asn Asn Val
385                 390                 395                 400
Ile Val Gly Asn Gln Ile Val Arg Arg Ala Val Asn Pro Lys Thr Arg
                405                 410                 415
Ile Leu Glu Tyr Thr Ile His Glu Leu Arg Asn Gly Ile Gln Leu Thr
            420                 425                 430
Glu Glu Gln Glu Ser Thr Glu Asn Ser Glu Pro Thr Val Thr Pro Gly
            435                 440                 445
Lys Asp Ile Tyr Asn Asp Val Leu Cys Ile Tyr Arg Ser Ile Phe Leu
450                 455                 460
```

```
Asp Tyr Pro Glu Ser Glu Met Val Glu Leu Ala Thr Gln Gly Val Leu
465                 470                 475                 480

Asp Ser Lys His Phe Ala Lys Glu Trp Pro Leu Gln Asp Glu Glu Glu
                485                 490                 495

His Leu Leu Thr Phe Ile Ile Lys Leu Met Pro Arg Leu Thr Phe Thr
            500                 505                 510

His Thr Asp Leu Glu Leu Lys Ser Asp Phe Met Pro Ser Gly Glu Val
        515                 520                 525

Val Val Leu Pro Leu His Thr Thr Ile Gly Glu Val Lys Glu Ala Ala
    530                 535                 540

Glu Lys Ala Leu Arg Asp Thr Tyr Tyr Val Thr Glu Gln Phe Glu Val
545                 550                 555                 560

Leu Ala Ile Glu Asn Leu Glu Asn Tyr Glu Asp Arg Glu Val Ile Phe
                565                 570                 575

Gly Ala Val Glu Ser Gly Ala Glu Leu Phe Val Lys Gly Met Gly Ile
            580                 585                 590

Asp Leu Asp Thr Pro Leu Lys Tyr Gln Gly Gly Val Gly Thr Trp Lys
        595                 600                 605

Val Arg Cys Glu Cys Gly Thr Gly Asp Asp Gly Glu Arg Met Val
    610                 615                 620

Ala Cys Asp Ile Cys Glu Ile Trp Gln His Thr Arg Cys Cys Gly Ile
625                 630                 635                 640

Asp Asp Ala Asp Asn Val Pro Leu Leu Phe Val Cys Ala Ala Cys Cys
                645                 650                 655

Asp Ser Leu Gly Gln Leu Lys Ile
            660

<210> SEQ ID NO 3
<211> LENGTH: 1995
<212> TYPE: DNA
<213> ORGANISM: Cucumis sativus

<400> SEQUENCE: 3
atgtcgattt cgattctgga atcctgcaag aagagaaaaa gaaggcctaa acttttcggg      60
tttcaaacgt tcggggatcc tggatcgcca atcaaccccA cgggtccatt tcgtgagaat     120
atcagaatct tcttcaaca atgtgcagag attgaagatt acagaattca agaaatgcct      180
atatggtgta ctctccttgt tcatgaaaat aaaagcttcg ttgttccact ttacactatt     240
gaagaagatg tgaagctctc cccaaaaccc tactgcgatc aatgccgatg ttctgggtgg     300
agtaatcatt ttgtatcgaa aagaaaatat catatcgtaa taccgttgga tgatcggtgg     360
aacaaacgat tagacgatgg cggtttcgac ctcgatgatc aaactcatct tcttcatgga     420
ttgattcact gcaatggctt cgggcatttg ctctgcgtca atggaatcga aggaggatcc     480
aagtttcttt gtggcagaga agttatggat ctttgggata gaatctgcac aaatctaaga     540
acaaggaaaa ttacagttga ggattatcc aagaaacgat caatggatct acgtcttctt      600
catggggtag catacggtca tccatggttt gggagatggg gctacagatt tgccgagga      660 agctttggag tgaaagaaca ccattacagt agagctttgg aaatcctcag ctctctggaa     720
ctcgacaaga taatgcacga agtcgactat agcgatcgag gaagagaagt gaagcaaatc     780
attcgacatt atcgaaatct gagtgaaacg cagttgatca cactgaaaga tctactgaag     840
ttcatgttga cagtaaaata tgtttctgcg atcgagaaga aaacggttca accaatcgct     900
aaatctcctc ctccgtgtag acaatctctg cagcgaaaca agcagcaatc tctagtgaag     960
```

-continued

```
gagaagcaaa tacggtacag aaaattcgcc actgcaattt ctaatatgga cagccgatgg    1020
ccggcgagac ggttagaata cgcagcggag gtgattgtga aagcattgga agagaagaaa    1080
tcagataaat tcagccatgg cggaaatgga atgactcgtc aagatgttcg agatgctgct    1140
cgccttcaca tcggcgacac tggattgctc gattacgttc taaaatcact gaacaacgtg    1200
atcgtaggta accaaatagt tcgccgtgca gtgaatccta aaacacgaat tttagaggac    1260
acgattcatg aacttagaaa tggcattcaa ttaacagaag agcaagaatc aacagaaaat    1320
tcagaaccaa ccgtaactcc tggcaaagac atttacaacg acgtgctatg tatatacaga    1380 agcatttttcc ttgactatcc agaatcagaa atggtagaat tagcaaccca gggagttctc    1440
gatagtaaac attttgctaa agaatggcct cttcaagatg aagaagagca tctattgacg    1500
ttcattatca aattgatgcc gaggctaact tttacacata cggatttaga gttgaagagt    1560
gatttcatgc catccggcga ggtagtggtt cttccactac acacaacaat cggagaagta    1620
aaagaagcag cagaaaaagc tctaagagac acatattacg ttacgaaaca gttcgaggtt    1680
ttggcgatag agaatttgga gaattacgaa gacagagagg tgattttttgg agcggtagaa    1740 tcgggagcag agttgtttgt gaaaggaatg ggtattgatt tagatacacc attgaagtac    1800
caaggaggag ttggtacatg gaaagttcga tgtgagtgtg gcaccggaga cgacgatggc    1860
gagaggatgg tggcttgtga catatgcgag atctggcagc acactcgctg ctgtggaatc    1920
gacgacgctg ataatgtgcc gttgttgttc gtatgcgccg cctgctgcga ctcgcttgga    1980
caattaaaaa tttga                                                    1995
```

<210> SEQ ID NO 4
<211> LENGTH: 664
<212> TYPE: PRT
<213> ORGANISM: Cucumis sativus

<400> SEQUENCE: 4

```
Met Ser Ile Ser Ile Leu Glu Ser Cys Lys Lys Arg Lys Arg Arg Pro
1               5                   10                  15

Lys Leu Phe Gly Phe Gln Thr Phe Gly Asp Pro Gly Ser Pro Ile Asn
            20                  25                  30

Pro Thr Gly Pro Phe Arg Glu Asn Ile Arg Ile Phe Leu Gln Gln Cys
        35                  40                  45

Ala Glu Ile Glu Asp Tyr Arg Ile Gln Glu Met Pro Ile Trp Cys Thr
    50                  55                  60

Leu Leu Val His Glu Asn Lys Ser Phe Val Val Pro Leu Tyr Thr Ile
65                  70                  75                  80

Glu Glu Asp Val Lys Leu Ser Pro Lys Pro Tyr Cys Asp Gln Cys Arg
                85                  90                  95

Cys Ser Gly Trp Ser Asn His Phe Val Ser Lys Arg Lys Tyr His Ile
            100                 105                 110

Val Ile Pro Leu Asp Asp Arg Trp Asn Lys Arg Leu Asp Asp Gly Gly
        115                 120                 125

Phe Asp Leu Asp Asp Gln Thr His Leu Leu His Gly Leu Ile His Cys
    130                 135                 140

Asn Gly Phe Gly His Leu Leu Cys Val Asn Gly Ile Glu Gly Gly Ser
145                 150                 155                 160

Lys Phe Leu Cys Gly Arg Glu Val Met Asp Leu Trp Asp Arg Ile Cys
                165                 170                 175

Thr Asn Leu Arg Thr Arg Lys Ile Thr Val Glu Asp Leu Ser Lys Lys
            180                 185                 190
```

```
Arg Ser Met Asp Leu Arg Leu Leu His Gly Val Ala Tyr Gly His Pro
        195                 200                 205
Trp Phe Gly Arg Trp Gly Tyr Arg Phe Cys Arg Gly Ser Phe Gly Val
    210                 215                 220
Lys Glu His His Tyr Ser Arg Ala Leu Glu Ile Leu Ser Ser Leu Glu
225                 230                 235                 240
Leu Asp Lys Ile Met His Glu Val Asp Tyr Ser Asp Arg Gly Arg Glu
                245                 250                 255
Val Lys Gln Ile Ile Arg His Tyr Arg Asn Leu Ser Glu Thr Gln Leu
                260                 265                 270
Ile Thr Leu Lys Asp Leu Leu Lys Phe Met Leu Thr Val Lys Tyr Val
        275                 280                 285
Ser Ala Ile Glu Lys Lys Thr Val Gln Pro Ile Ala Lys Ser Pro Pro
        290                 295                 300
Pro Cys Arg Gln Ser Leu Gln Arg Asn Lys Gln Gln Ser Leu Val Lys
305                 310                 315                 320
Glu Lys Gln Ile Arg Tyr Arg Lys Phe Ala Thr Ala Ile Ser Asn Met
                325                 330                 335
Asp Ser Arg Trp Pro Ala Arg Arg Leu Glu Tyr Ala Ala Glu Val Ile
                340                 345                 350
Val Lys Ala Leu Glu Glu Lys Lys Ser Asp Lys Phe Ser His Gly Gly
                355                 360                 365
Asn Gly Met Thr Arg Gln Asp Val Arg Asp Ala Ala Arg Leu His Ile
        370                 375                 380
Gly Asp Thr Gly Leu Leu Asp Tyr Val Leu Lys Ser Leu Asn Asn Val
385                 390                 395                 400
Ile Val Gly Asn Gln Ile Val Arg Arg Ala Val Asn Pro Lys Thr Arg
                405                 410                 415
Ile Leu Glu Asp Thr Ile His Glu Leu Arg Asn Gly Ile Gln Leu Thr
                420                 425                 430
Glu Glu Gln Glu Ser Thr Glu Asn Ser Glu Pro Thr Val Thr Pro Gly
                435                 440                 445
Lys Asp Ile Tyr Asn Asp Val Leu Cys Ile Tyr Arg Ser Ile Phe Leu
        450                 455                 460
Asp Tyr Pro Glu Ser Glu Met Val Glu Leu Ala Thr Gln Gly Val Leu
465                 470                 475                 480
Asp Ser Lys His Phe Ala Lys Glu Trp Pro Leu Gln Asp Glu Glu Glu
                485                 490                 495
His Leu Leu Thr Phe Ile Ile Lys Leu Met Pro Arg Leu Thr Phe Thr
                500                 505                 510
His Thr Asp Leu Glu Leu Lys Ser Asp Phe Met Pro Ser Gly Glu Val
                515                 520                 525
Val Val Leu Pro Leu His Thr Thr Ile Gly Glu Val Lys Glu Ala Ala
        530                 535                 540
Glu Lys Ala Leu Arg Asp Thr Tyr Tyr Val Thr Glu Gln Phe Glu Val
545                 550                 555                 560
Leu Ala Ile Glu Asn Leu Glu Asn Tyr Glu Asp Arg Glu Val Ile Phe
                565                 570                 575
Gly Ala Val Glu Ser Gly Ala Glu Leu Phe Val Lys Gly Met Gly Ile
                580                 585                 590
Asp Leu Asp Thr Pro Leu Lys Tyr Gln Gly Gly Val Gly Thr Trp Lys
        595                 600                 605
```

Val Arg Cys Glu Cys Gly Thr Gly Asp Asp Asp Gly Glu Arg Met Val
    610                 615                 620

Ala Cys Asp Ile Cys Glu Ile Trp Gln His Thr Arg Cys Cys Gly Ile
625                 630                 635                 640

Asp Asp Ala Asp Asn Val Pro Leu Leu Phe Val Cys Ala Ala Cys Cys
                645                 650                 655

Asp Ser Leu Gly Gln Leu Lys Ile
            660

```
<210> SEQ ID NO 5
<211> LENGTH: 29
<212> TYPE: DNA
<213> ORGANISM: Artificial Sequence
<220> FEATURE:
<223> OTHER INFORMATION: Synthetic primer

<400> SEQUENCE: 5
aattacatga ataagtgttc gtaatttcg                                    29

<210> SEQ ID NO 6
<211> LENGTH: 29
<212> TYPE: DNA
<213> ORGANISM: Artificial Sequence
<220> FEATURE:
<223> OTHER INFORMATION: Synthetic primer

<400> SEQUENCE: 6
aattacatga ataagtgttc gtaatttcc                                    29

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
ggtttggaat cttgcttggc attg                                         24

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8
ggtttggaat cttgcttggc attc                                         24

<210> SEQ ID NO 9
<211> LENGTH: 30
<212> TYPE: DNA
<213> ORGANISM: Artificial Sequence
<220> FEATURE:
<223> OTHER INFORMATION: Synthetic primer

<400> SEQUENCE: 9
atctagaaac caaataaaaa ctatagccaa                                   30

<210> SEQ ID NO 10
<211> LENGTH: 28
<212> TYPE: DNA
<213> ORGANISM: Artificial Sequence
<220> FEATURE:
<223> OTHER INFORMATION: Synthetic primer
```

-continued

<400> SEQUENCE: 10
ctagaaacca aataaaaact atagccag                                          28

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
ggaacccctt ctgaagctgt g                                                 21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
ggaacccctt ctgaagctgt c                                                 21

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
gggtcacgca gatgggtatt ga                                                22

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
ggtcacgcag atgggtattg g                                                 21

<210> SEQ ID NO 15
<211> LENGTH: 30
<212> TYPE: DNA
<213> ORGANISM: Artificial Sequence
<220> FEATURE:
<223> OTHER INFORMATION: Synthetic primer

<400> SEQUENCE: 15
atttggtttc ttgatactat caattatacc                                        30

<210> SEQ ID NO 16
<211> LENGTH: 30
<212> TYPE: DNA
<213> ORGANISM: Artificial Sequence
<220> FEATURE:
<223> OTHER INFORMATION: Synthetic primer

<400> SEQUENCE: 16
atttggtttc ttgatactat caattatacg                                        30

<210> SEQ ID NO 17

```
<211> LENGTH: 32
<212> TYPE: DNA
<213> ORGANISM: Artificial Sequence
<220> FEATURE:
<223> OTHER INFORMATION: Synthetic primer

<400> SEQUENCE: 17
tacgtgaata ttttcttttt ctttatacgt at                             32

<210> SEQ ID NO 18
<211> LENGTH: 30
<212> TYPE: DNA
<213> ORGANISM: Artificial Sequence
<220> FEATURE:
<223> OTHER INFORMATION: Synthetic primer

<400> SEQUENCE: 18
cgtgaatatt ttcttttct ttatacgtag                                30

<210> SEQ ID NO 19
<211> LENGTH: 26
<212> TYPE: DNA
<213> ORGANISM: Artificial Sequence
<220> FEATURE:
<223> OTHER INFORMATION: Synthetic primer

<400> SEQUENCE: 19
aagactaata tgcccttcct cttcta                                   26

<210> SEQ ID NO 20
<211> LENGTH: 24
<212> TYPE: DNA
<213> ORGANISM: Artificial Sequence
<220> FEATURE:
<223> OTHER INFORMATION: Synthetic primer

<400> SEQUENCE: 20
gactaatatg cccttcctct tctg                                     24

<210> SEQ ID NO 21
<211> LENGTH: 25
<212> TYPE: DNA
<213> ORGANISM: Artificial Sequence
<220> FEATURE:
<223> OTHER INFORMATION: Synthetic primer

<400> SEQUENCE: 21
tatgtacagc atcaacaagt gtgca                                    25

<210> SEQ ID NO 22
<211> LENGTH: 23
<212> TYPE: DNA
<213> ORGANISM: Artificial Sequence
<220> FEATURE:
<223> OTHER INFORMATION: Synthetic primer

<400> SEQUENCE: 22
tgtacagcat caacaagtgt gcc                                      23

<210> SEQ ID NO 23
<211> LENGTH: 32
<212> TYPE: DNA
<213> ORGANISM: Artificial Sequence
<220> FEATURE:
<223> OTHER INFORMATION: Synthetic primer

<400> SEQUENCE: 23
```

```
ttcgaacata tacaaaagta gatatatcaa aa                              32

<210> SEQ ID NO 24
<211> LENGTH: 30
<212> TYPE: DNA
<213> ORGANISM: Artificial Sequence
<220> FEATURE:
<223> OTHER INFORMATION: Synthetic primer

<400> SEQUENCE: 24
cgaacatata caaaagtaga tatatcaaac                                 30

<210> SEQ ID NO 25
<211> LENGTH: 31
<212> TYPE: DNA
<213> ORGANISM: Artificial Sequence
<220> FEATURE:
<223> OTHER INFORMATION: Synthetic primer

<400> SEQUENCE: 25
aaacttcaag tttaggatag aatcggtttg a                               31

<210> SEQ ID NO 26
<211> LENGTH: 35
<212> TYPE: DNA
<213> ORGANISM: Artificial Sequence
<220> FEATURE:
<223> OTHER INFORMATION: Synthetic primer

<400> SEQUENCE: 26
caatcaacca tattcagttt aatcaactaa acaaa                           35

<210> SEQ ID NO 27
<211> LENGTH: 44
<212> TYPE: DNA
<213> ORGANISM: Artificial Sequence
<220> FEATURE:
<223> OTHER INFORMATION: Synthetic primer

<400> SEQUENCE: 27
aatttagttt caaatttgt ttattaataa aaatatacat ctct                  44

<210> SEQ ID NO 28
<211> LENGTH: 25
<212> TYPE: DNA
<213> ORGANISM: Artificial Sequence
<220> FEATURE:
<223> OTHER INFORMATION: Synthetic primer

<400> SEQUENCE: 28
gtagctataa gaaagggcag agacc                                      25

<210> SEQ ID NO 29
<211> LENGTH: 28
<212> TYPE: DNA
<213> ORGANISM: Artificial Sequence
<220> FEATURE:
<223> OTHER INFORMATION: Synthetic primer

<400> SEQUENCE: 29
tccaatcacc acttcctaca atttatcg                                   28

<210> SEQ ID NO 30
<211> LENGTH: 32
<212> TYPE: DNA
```

```
<213> ORGANISM: Artificial Sequence
<220> FEATURE:
<223> OTHER INFORMATION: Synthetic primer

<400> SEQUENCE: 30
caaatgttgg acaacaacat gatatttagt ag                          32

<210> SEQ ID NO 31
<211> LENGTH: 34
<212> TYPE: DNA
<213> ORGANISM: Artificial Sequence
<220> FEATURE:
<223> OTHER INFORMATION: Synthetic primer

<400> SEQUENCE: 31
atttagaaaa cacacgtatc aaaattaact tagc                        34

<210> SEQ ID NO 32
<211> LENGTH: 28
<212> TYPE: DNA
<213> ORGANISM: Artificial Sequence
<220> FEATURE:
<223> OTHER INFORMATION: Synthetic primer

<400> SEQUENCE: 32
attccaagtt gggattgaat ggaaatgg                               28

<210> SEQ ID NO 33
<211> LENGTH: 31
<212> TYPE: DNA
<213> ORGANISM: Artificial Sequence
<220> FEATURE:
<223> OTHER INFORMATION: Synthetic primer

<400> SEQUENCE: 33
atcatctgtc tccaattcac ttgaaaactt t                           31

<210> SEQ ID NO 34
<211> LENGTH: 35
<212> TYPE: DNA
<213> ORGANISM: Artificial Sequence
<220> FEATURE:
<223> OTHER INFORMATION: Synthetic primer

<400> SEQUENCE: 34
gtgattcatt gagaatatct atttaattgt acttg                       35
```